(12) United States Patent
Aller

(10) Patent No.: US 7,774,070 B2
(45) Date of Patent: Aug. 10, 2010

(54) MEDICAL ELECTRODE ASSEMBLY FOR ELECTROTHERAPY AND PHOTOTHERAPY TREATMENT

(75) Inventor: Brady Aller, West Chester, PA (US)

(73) Assignee: Hill Laboratories Company, Frazer, PA (US)

( * ) Notice: Subject to any disclaimer, the term of this patent is extended or adjusted under 35 U.S.C. 154(b) by 0 days.

(21) Appl. No.: 11/972,022

(22) Filed: Jan. 10, 2008

(65) Prior Publication Data

US 2009/0182396 A1 Jul. 16, 2009

(51) Int. Cl.
*A61N 1/04* (2006.01)

(52) U.S. Cl. .................. 607/115; 607/117; 607/88; 607/89; 606/2

(58) Field of Classification Search .............. 606/1–14; 607/88, 89, 90, 115–117
See application file for complete search history.

(56) References Cited

U.S. PATENT DOCUMENTS

| | | | |
|---|---|---|---|
| 4,300,575 A | 11/1981 | Wilson | |
| 4,391,278 A | 7/1983 | Cahalan et al. | |
| 4,539,995 A | 9/1985 | Segawa | |
| 4,674,511 A | 6/1987 | Cartmell | |
| 4,685,467 A | 8/1987 | Cartmell et al. | |
| 4,694,835 A | 9/1987 | Strand | |
| 4,800,887 A | 1/1989 | Shigeta et al. | |
| 4,838,273 A | 6/1989 | Cartmell | |
| 5,133,356 A | 7/1992 | Bryan et al. | |
| 5,197,472 A | 3/1993 | DiSabito | |
| 5,215,087 A | 6/1993 | Anderson et al. | |
| 5,226,225 A | 7/1993 | Bryan et al. | |
| 5,265,579 A | 11/1993 | Ferrari | |
| 5,356,428 A | 10/1994 | Way | |
| 5,450,845 A | 9/1995 | Axelgaard | |
| 5,474,528 A * | 12/1995 | Meserol | 604/20 |
| 5,499,628 A | 3/1996 | Wright | |
| 5,505,726 A * | 4/1996 | Meserol | 606/9 |
| 5,571,165 A * | 11/1996 | Ferrari | 607/142 |
| 5,785,040 A | 7/1998 | Axelgaard | |
| 6,600,957 B2 | 7/2003 | Gadsby | |
| 6,907,299 B2 | 6/2005 | Han | |
| 6,999,822 B2 | 2/2006 | Koike | |
| 7,004,174 B2 * | 2/2006 | Eggers et al. | 128/898 |
| 7,271,375 B2 * | 9/2007 | Gidon et al. | 250/208.1 |
| 7,304,201 B2 * | 12/2007 | Holloway et al. | 602/41 |
| 2002/0068861 A1 | 6/2002 | Yang | |
| 2002/0196036 A1 * | 12/2002 | Toyoshima et al. | 324/702 |
| 2004/0088036 A1 * | 5/2004 | Gilbert | 607/148 |
| 2004/0136634 A1 * | 7/2004 | Chowdhury et al. | 385/3 |
| 2004/0166146 A1 * | 8/2004 | Holloway et al. | 424/449 |
| 2004/0260376 A1 | 12/2004 | Craige, III et al. | |
| 2005/0010161 A1 | 1/2005 | Sun et al. | |
| 2006/0034499 A1 * | 2/2006 | Shinoda et al. | 382/124 |

(Continued)

*Primary Examiner*—Henry M Johnson, III
*Assistant Examiner*—Jeffrey B Lipitz
(74) *Attorney, Agent, or Firm*—Howson & Howson LLP

(57) ABSTRACT

A method for combining the effective modalities of electrotherapy and phototherapy is provided. A medical electrode assembly is substantially transparent or translucent to visible, infrared and/or ultraviolet light so that light rays emitted by a phototherapy device can shine through and pass transversely across every layer of the medical electrode assembly to impinge upon the skin of the patient to which the assembly is attached. This includes an area of skin located directly underneath the medical electrode assembly and thereby enables the combination therapy to be achieved.

13 Claims, 2 Drawing Sheets

U.S. PATENT DOCUMENTS

| | | | |
|---|---|---|---|
| 2006/0084938 A1* | 4/2006 | Zhang et al. | 604/501 |
| 2006/0122298 A1* | 6/2006 | Menon et al. | 524/318 |
| 2006/0161143 A1* | 7/2006 | Altshuler et al. | 606/9 |
| 2006/0183989 A1 | 8/2006 | Healy | |
| 2007/0032719 A1 | 2/2007 | Menon et al. | |
| 2007/0232962 A1* | 10/2007 | Zumeris et al. | 601/2 |
| 2007/0233208 A1* | 10/2007 | Kurtz et al. | 607/88 |
| 2007/0293793 A1* | 12/2007 | Johnson | 601/15 |
| 2008/0195089 A1* | 8/2008 | Thiagalingam et al. | 606/35 |

* cited by examiner

MEDICAL ELECTRODE ASSEMBLY FOR ELECTROTHERAPY AND PHOTOTHERAPY TREATMENT

BACKGROUND OF THE INVENTION

The present invention relates to the therapeutic application of electrotherapy and the therapeutic application of phototherapy to a patient, and more particularly, the present invention relates to a medical electrode assembly for use in applying these therapies and a method in which the therapies can be applied to a patient simultaneously.

Phototherapy and electrotherapy are two very different therapies. Phototherapy is a process where light and/or laser photons are directed onto the skin of the patient and enter the tissue of the skin of the patient for therapeutic purposes. The phototherapy light source is typically provided by a pad with a cluster of LEDs or a probe with LEDs and/or lasers or other light source. U.S. Patent Application Publication No. 2004/0166146 A1 of Holloway et al. provides an example of the use of phototherapy.

In contrast, electrotherapy is the therapeutic application of electricity to the body. Stimulation wires have one end electrically connected to an electrical stimulation machine and the other end electrically connected to the skin of the body. Single or multiple channels with various frequencies can be utilized. Medical electrodes assemblies are used to connect the stimulation wires to the skin of the patient's body and are typically made of at least three separate layers. The three layers include an adhesive layer used to attach the medical electrode assembly to the body, a black rubber layer secured over the adhesive layer, and a foam or cloth backing layer attached to the rubber layer. Such medical electrode assemblies are not transparent with respect to visible, ultraviolet or infrared light, and one cannot visually see the skin of the patient through the electrode assembly.

U.S. Pat. Nos. 5,450,845 and 5,785,040 issued to Axelgaard provide examples of the construction of a typical medical electrode assembly. Also see U.S. Patent Application Publication No. 2005/0010161 A1 of Sun et al. for applying electricity or light to the skin of a patient. Further, see U.S. Patent Application Publication No. 2002/0068861 A1 of Yang and U.S. Pat. No. 4,539,995 issued to Segawa, U.S. Pat. Nos. 4,674,511 and 4,838,273 issued to Cartrnell, U.S. Pat. No. 4,685,467 issued to Cartnell et al., U.S. Pat. No. 4,800,887 issued to Shigeta et al., U.S. Pat. Nos. 5,265,579 and 5,571,165 issued to Ferrari, U.S. Pat. No. 5,356,428 issued to Way, U.S. Pat. No. 5,499,628 issued to Wright, and U.S. Pat. No. 6,600,957 B2 issued to Gadsby for medical electrode assemblies that are radiolucent or transparent with respect to x-rays. U.S. Pat. No. 4,300,575 issued to Wilson, U.S. Pat. No. 6,907,299 B2 issued to Han, U.S. Pat. No. 6,999,822 B2 issued to Koike, U.S. Pat. No. 4,391,278 issued to Cahalan et al., U.S. Pat. No. 4,694,835 issued to Strand, U.S. Pat. Nos. 5,133,356 and 5,226,225 issued to Bryan et al., and U.S. Pat. No. 5,215,087 issued to Anderson et al. and U.S. Patent Application Publication No. 2006/0183989 A1 of Healy disclose other medical electrode assemblies.

While the medical electrode assemblies and/or methods of use disclosed in the above referenced patents and published applications may function in a satisfactory manner for their intended purposes, there remains a need for a method of treatment and medical electrode assembly enabling the simultaneous therapeutic applications of electrotherapy and phototherapy to a patient.

SUMMARY OF THE INVENTION

The present invention provides a method for combining the two above referenced very effective modalities of electrotherapy and phototherapy. It is submitted that the combination of electrotherapy and phototherapy will have advanced synergistic effects since these therapies have proven therapeutic effectiveness when used alone. The present invention also provides a medical electrode assembly. Substantially the entire medical electrode assembly is transparent or translucent so that the radiation or light rays emitted by a phototherapy device shines and passes through the medical electrode assembly and is applied to the skin of the patient, including skin located directly underneath the medical electrode assembly, to achieve the combination therapy.

Preferably, the medical electrode assembly according to the present invention comprises or consists of an upper flexible gel layer secured over a lower flexible gel layer with an exposed end of an electrically-conductive lead wire sandwiched therebetween. The lower flexible gel layer is electrically conductive for electrically coupling the assembly to the skin of the patient and is self-adhesive for adhering the assembly to the skin of the patient. Both the upper and lower flexible gel layers are transparent or translucent relative to visible, ultraviolet and/or infrared light to permit passage or transmission of visible, ultraviolet and/or infrared light rays through the assembly.

Preferably, the method of therapy using the medical electrode assembly of the present invention comprises the steps of adhering the medical electrode assembly to the skin of patient and applying electrotherapy to a patient via the medical electrode assembly while simultaneously applying phototherapy to the skin of the patient with a light source. The step of applying phototherapy preferably includes directing visible, ultraviolet and/or infrared light emitted by the phototherapy light source through the medical electrode assembly and onto the skin of the patient including the skin of the patient located directly underneath the medical electrode assembly.

In one contemplated embodiment, the light source emits electromagnetic radiation within a wavelength range of 280 nm to 50,000 nm, and the medical electrode assembly includes upper and lower flexible transparent layers that are transparent or translucent to, and permit passage of, electromagnetic radiation of a wavelength of 280 nm to 50,000 nm. In another contemplated embodiment, the light source emits electromagnetic radiation within a wavelength range of 400 nm to 1,000 nm, and the upper and lower flexible transparent layers are transparent or translucent to, and permit passage of, electromagnetic radiation of a wavelength of 400 nm to 1,000 nm.

BRIEF DESCRIPTION OF THE DRAWINGS

The features and advantages of the present invention should become apparent from the following description when taken in conjunction with the accompanying drawings, in which.

DETAILED DESCRIPTION OF THE INVENTION

Figure 1:
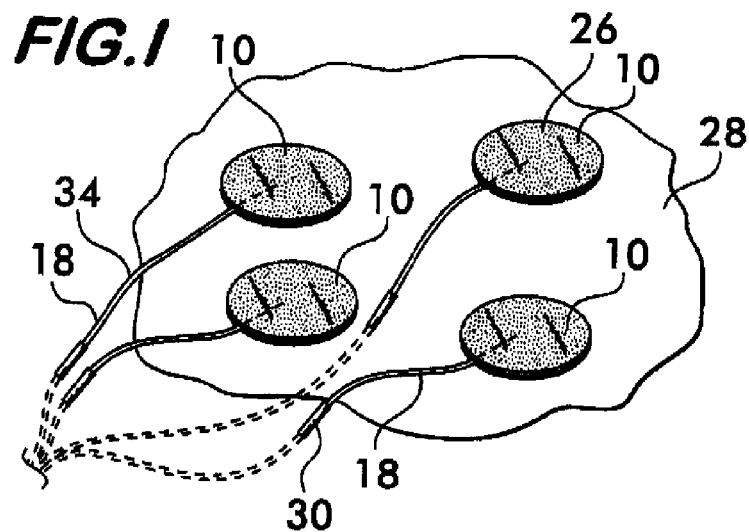
FIG. 1 is a perspective view of a series of separate medical electrode assemblies adhered to a release sheet according to the present invention.
Figure 2:
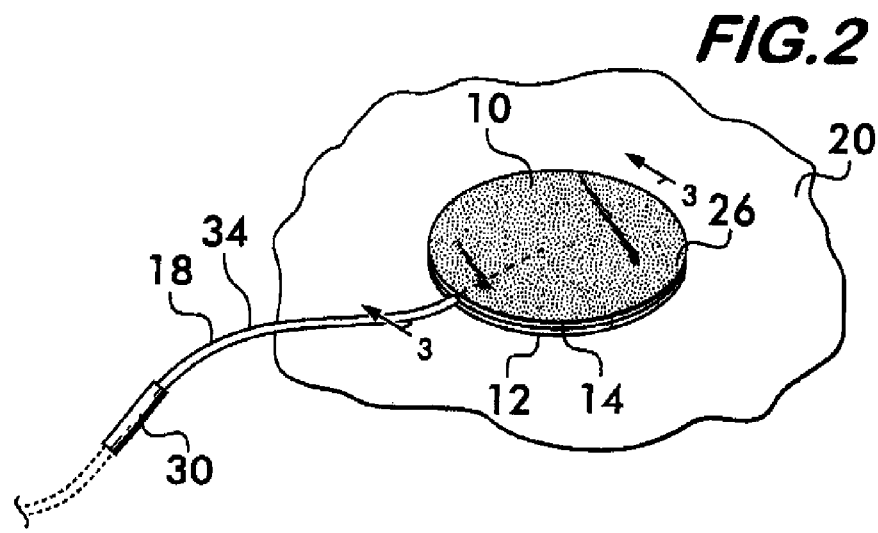
FIG. 2 is a perspective view of a single medical electrode assembly adhered to the skin of a patient according to the present invention.
Figure 3:
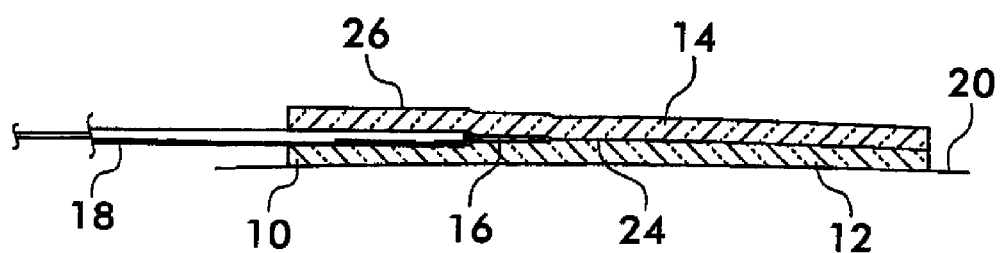
FIG. 3 is a cross-sectional view of the medical electrode assembly taken along line 3-3.

FIGS. 1-3 illustrate the medical electrode assembly 10 according to the present invention. The assembly includes dual layers, 12 and 14, that can be provided as patches, pads, or the like and be of substantially any size desired. The assembly 10 can include more than two layers; however, in its preferred embodiment, the assembly 10 of the present invention consists of a pair of opposed continuous layers. A free exposed end 16 of carbon fiber, steel fiber, copper fiber or any other type of electrically-conductive stimulation lead wire 18 is attached to the assembly 10 by being secured and sandwiched between the dual layers, 12 and 14.

Figure 4:
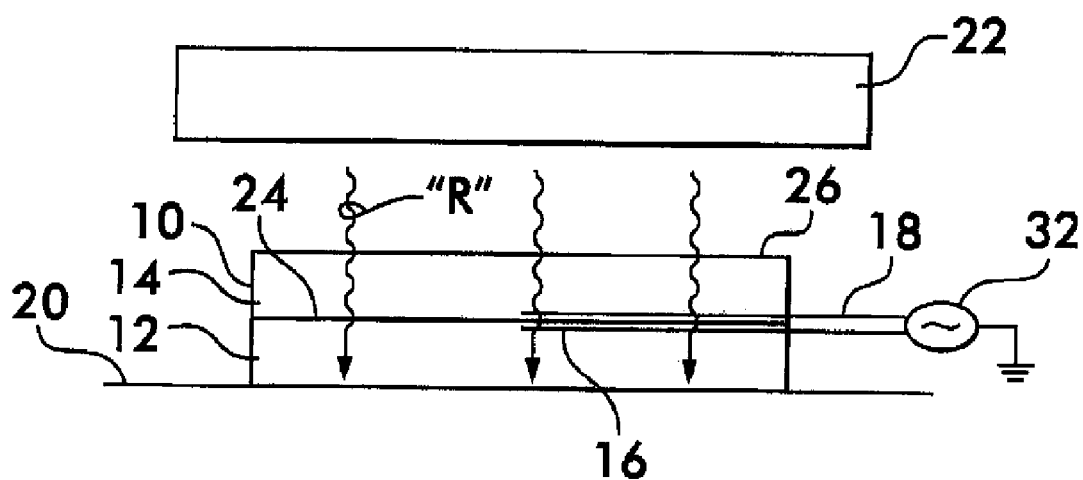
FIG. 4 is a schematic view of a first embodiment of a combination of a medical electrode assembly and a light source according to the present invention.
Figure 5:
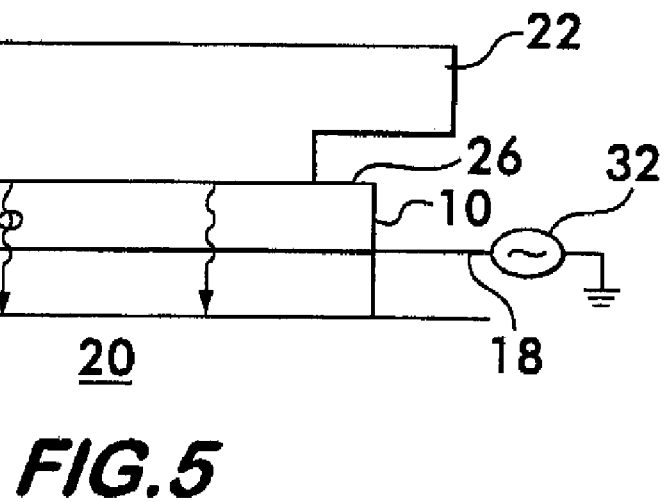
FIG. 5 is a schematic view of a second embodiment of a combination of a medical electrode assembly and a light source according to the present invention.

Both of the dual layers, 12 and 14, are transparent or translucent to visible light, ultraviolet light, and/or infrared light. For example, with respect to the preferred embodiment, the dual layers, 12 and 14, are substantially clear and a person can visual see directly through the dual layers, 12 and 14, to objects located on the other side of the dual layers, 12 and 14. Preferably, each of the dual layers, 12 and 14, are continuously transparent or translucent throughout their entire body so as not to block, absorb, reflect, or prevent substantially any transmission of light through any part of the assembly 10 and therefore, enable maximum passage of light to the patient's skin 20 lying directly underneath the assembly 10. The only exception is the relatively small and thin lead wire 18 which may not be transparent and may absorb and/or reflect rays of light. Otherwise, the entire assembly 10 is transparent or translucent to light and permits light rays "R" emitted by a phototherapy device, or light source, 22 to shine through the layers, 12 and 14, onto the skin 20 of the patient. See FIGS. 4 and 5.

Preferably, the dual layers, 12 and 14, include a lower flexible layer 12 intended to engage the skin 20 of the patient and an upper flexible layer 14 that faces outward of the skin 20 toward the phototherapy, or light source, device 22. The flexibility of the layers 12 and 14 enable the assembly 10 to conform to the contour of the skin 20 on which it is attached. Flexibility is particularly important for relatively large assemblies having a relatively large surface area. Alternatively, the layers, 12 and 14, can be substantially rigid if the assembly is relatively small and has only a small surface area.

As an example, the lower layer 12 can be a sticky, tacky, or self-adhesive gel-like substance. Such a gel layer 12 can be electrically-conductive such that it electrically couples the lead wire 18 to the skin 20. In addition, the gel layer 12 can have an exterior relative-tacky surface enabling the gel layer 12 to be removably self-adhered directly to the skin 22 of the patient. The upper face 24 of the gel layer 12 can also be tacky for purposes of self-adhering the lead wire 18 thereto and for adhering the upper layer 14 thereto. Alternatively, separate adhesive layers can be used.

The upper flexible layer 14 can be made of the same gel material as the lower flexible layer 12. If desired, the upper gel layer 14 can made of a conductive gel material, or more preferably, a non-conductive gel material. Its surfaces can be tacky to enable it to form a strong bond with the lower gel layer 12 and lead wire 18. Its upper face 26 can also be tacky to enable the separate phototherapy, or light source, device 22 to be removably adhered thereto. See FIG. 5. Alternatively, the upper layer 14 may not have a self-adherent property.

Preferably, the assembly 10 is provided as a disposable medical electrode assembly. For instance, as best illustrated in FIG. 1, the assembly 10 can initially be provided on a release sheet 28 that can be peeled away from the underside of the assembly 10. Also, the lead wire 18 can have a proximal free end forming a connection tip 30. In this manner, a lead wire of an electrical stimulation device 32 can be connected to tip 30. However, when discarding a used assembly 10, the assembly can be disconnected and only the short portion 34 of the lead wire need be discarded.

A method of treatment according to the present invention includes adhering lower layer 12 to the skin 20 of the patient. The proximal end of the lead wire 18 can be electrically connected to the electrical stimulation device 32 for electrically stimulating the patient via the medical electrode assembly 10. As an example, electrotherapy is typically given for about a period of 8 to 12 minutes depending upon the purpose of the application.

Simultaneously with the electrotherapy treatment, a phototherapy light source 22 can be used to provide phototherapy to the skin 22 of the patient, including the skin located directly underneath the medical electrode assembly. Phototherapy treatment typically is longer in duration then electrotherapy treatment. Thus, there may be periods of time where only phototherapy treatment or only electrotherapy treatment is applied. However, the use of the medical electrode assembly 10 enables the treatments to be applied simultaneously or sequentially without any disconnection or re-connection of the electrode assembly to the patient.

According to one contemplated embodiment, the phototherapy light source 22 comprises a small lightweight light emitting diode (LED) cluster that can be adhered directly to the upper tacky face 26 of the upper layer 14 of the assembly 10. Thus a phototherapy treatment and an electrotherapy treatment can be given simultaneously to substantially the same region of the body. Alternatively, the light source can be a large bank of lights not supported on the assembly or connected to the assembly.

The type of light rays used during phototherapy depends upon the purpose of the application. Visible or optical light having a wavelength of about 400 nm to 700 nm could be used, and the assembly 10 could permit such electromagnetic radiation to pass through the layers, 12 and 14, of the assembly. Alternatively, ultraviolet rays could be used, including UV-A, UV-B, or UV-C rays. This would correspond to electromagnetic radiation of a wavelength within the range of about 10 to 400 nm. Still further, infrared rays could be used, including near or far infrared. This would correspond to electromagnetic radiation of a wavelength within the range of about 700 nm to 1,000,000 nm. According to one contemplated embodiment the medical electrode assembly would permit passage of light rays having a wavelength of between 280 nm to 50,000 nm, or alternatively, between 400 nm and 1000 nm.

While preferred electrodes and methods of treatment have been described in detail, various modifications, alterations, and changes may be made without departing from the spirit and scope of the electrode assembly and method according to the present invention as defined in the appended claims.

The invention claimed is:

1. A medical electrode assembly for being applied to a patient's skin for simultaneously applying electrotherapy and phototherapy to the skin of the patient directly underlying the electrode assembly, comprising:

an upper flexible gel layer secured over a lower flexible gel layer with an exposed end of an electrically-conductive lead wire sandwiched therebetween;

said upper flexible gel layer forming an uppermost exposed surface of the medical electrode assembly;

said electrically-conductive lead wire having an opposite end for electrical connecting to a separate electrical stimulation device;

said lower flexible gel layer being electrically conductive and forming a lowermost surface of the medical electrode assembly adapted to directly engage the skin of the patient for electrically coupling the assembly to the skin of the patient and being self-adhesive for adhering the assembly to the skin of the patient; and said upper and lower flexible gel layers being made of the same gel material, being transparent or translucent to, and permitting passage of, at least one of visible light, ultraviolet light, and infrared light, and being continuously transparent or translucent throughout their entire bodies so as not to block, absorb, reflect, or prevent substantially any transmission of light through, any part of the assembly thereby enabling maximum passage of light through the assembly.

2. A medical electrode assembly according to claim 1, further comprising a light source for emitting one of visible light, ultraviolet light, and infrared light through the upper and lower flexible gel layers including through said uppermost exposed surface of the medical electrode assembly and onto the skin of the patient directly underlying the medical electrode assembly thereby enabling simultaneous application of electrotherapy via the electrically conductive lower gel layer and phototherapy via said light source through said transparent upper and lower layers to the skin of the patient underlying the medical electrode.

3. A medical electrode assembly according to claim 2, wherein said light source is removably secured to said upper flexible gel layer.

4. A medical electrode assembly according to claim 3, wherein said upper gel layer is self-adhesive for adhering said light source to said upper gel layer.

5. A medical electrode assembly according to claim 2, wherein said light source emits electromagnetic radiation within a wavelength range of 280 nm to 50,000 nm, and wherein said upper and lower flexible gel layers are transparent or translucent to, and permit passage of electromagnetic radiation of a wavelength of 280 nm to 50,000 nm.

6. A medical electrode assembly according to claim 2, wherein said light source emits electromagnetic radiation within a wavelength range of 400 nm to 1,000 nm, and wherein said upper and lower flexible gel layers are transparent or translucent to, and permit passage of, electromagnetic radiation of a wavelength of 400 nm to 1,000 nm.

7. A medical electrode assembly for being applied to a patient's skin for simultaneously applying electrotherapy and phototherapy to the skin of the patient directly underlying the electrode assembly, consisting of:

an upper flexible layer forming an uppermost exposed surface of said electrode assembly;

a lower flexible electrically-conductive layer secured to said upper layer for forming a two-layer electrode assembly, said lower layer forming a lowermost surface of the medical electrode assembly adapted to directly engage the skin of the patient; and an electrically-conductive lead wire having an exposed end sandwiched between said upper and lower layers and an opposite end for being electrically connected to a separate electrical stimulation device;

said upper and lower flexible layers being made of the same gel material, being transparent or translucent to, and permitting passage of, at least one of visible light, ultraviolet light, and infrared light, and being continuously transparent or translucent throughout their entire bodies so as not to block absorb, reflect, or prevent substantially any transmission of light through any part of the assembly thereby enabling maximum passage of light through the assembly.

8. A medical electrode assembly according to claim 7, wherein said lower layer is an electrically-conductive, self-adhesive gel for electrically coupling the assembly to the skin of the patient and for adhering the assembly to the skin of the patient.

9. A medical electrode assembly according to claim 8, wherein said medical electrode assembly is provided in combination with:

a separate light source for emitting light through the upper and lower flexible layers of said medical electrode assembly and onto the skin of the patient directly underlying said medical electrode assembly, said light source being one of a visible light source for emitting visible light, an ultraviolet light source for emitting ultraviolet light, and an infrared light source for emitting infrared light; and an electrical stimulation device electrically connected to said opposite end of said lead wire for electrically stimulating the skin of a patient underlying the electrode assembly via the electrically-conductive lower layer of the electrode assembly.

10. A medical electrode assembly according to claim 9, wherein said light source is removably secured to said upper flexible layer.

11. A medical electrode assembly according to claim 10, wherein said upper flexible layer is a self-adhesive gel for adhering said light source to said upper layer.

12. A medical electrode assembly according to claim 9, wherein said light source emits electromagnetic radiation within a wavelength range of 280 nm to 50,000 nm, and wherein said upper and lower flexible layers are transparent or translucent to, and permit passage of electromagnetic radiation of a wavelength of 280 nm to 50,000 nm.

13. A medical electrode assembly according to claim 9, wherein said light source emits electromagnetic radiation within a wavelength range of 400 nm to 1,000 nm, and wherein said upper and lower flexible layers are transparent or translucent to, and permit passage of, electromagnetic radiation of a wavelength of 400 nm to 1,000 nm.

* * * * *